(12) United States Patent
Gugel (10) Patent No.: US 8,263,946 B2
(45) Date of Patent: Sep. 11, 2012

(54) METHOD AND APPARATUS FOR HIGH-RESOLUTION OPTICAL SCANNING OF A SAMPLE

(75) Inventor: Hilmar Gugel, Dossenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 665 days.

(21) Appl. No.: 12/444,572

(22) PCT Filed: Aug. 9, 2007

(86) PCT No.: PCT/EP2007/058291
§ 371 (c)(1),
(2), (4) Date: Jul. 13, 2009

(87) PCT Pub. No.: WO2008/040590
PCT Pub. Date: Apr. 10, 2008

(65) Prior Publication Data
US 2010/0006772 A1    Jan. 14, 2010

(30) Foreign Application Priority Data
Oct. 7, 2006   (DE) .................. 10 2006 047 816

(51) Int. Cl.
*G01N 21/64* (2006.01)

(52) U.S. Cl. .................................. 250/459.1

(58) Field of Classification Search ......... 250/459.1
See application file for complete search history.

(56) References Cited

U.S. PATENT DOCUMENTS
2004/0065845 A1    4/2004  Seyfried
2007/0023686 A1*   2/2007  Wolleschensky et al. . 250/458.1

FOREIGN PATENT DOCUMENTS
| DE | 10228374 | 1/2004 |
| DE | 10313138 | 10/2004 |
| DE | 10 2006 011 556 | 3/2007 |
| WO | 2005/040771 | 5/2005 |

OTHER PUBLICATIONS

ATTO-TEC GmbH ATTO 532 Product Information (Jan. 2004), 2 pages.*
Molecular Probes, Inc. FluoSpheres® Fluorescent Microspheres Product Information (Oct. 2005), 6 pages.*
Donnert et al. Macromolecular-scale resolution in biological fluorescence microscopy, PNAS vol. 103, No. 31 (Jul. 2006) pp. 11440-11445.*
Donnert et al. Two-color far-field fluorescence nanoscopy, Biophysical Journal vol. 92, No. 8 (Apr. 2007) pp. L67-L69.*

(Continued)

*Primary Examiner* — David Porta
*Assistant Examiner* — Shun Lee
(74) *Attorney, Agent, or Firm* — Schlee IP International, P.C.; Alexander R. Schlee (57) ABSTRACT

A method and an apparatus are suggested for high-resolution optical scanning, particularly in a laser scanning fluorescence microscope. A sample to be scanned comprises a first and a second substance that are switchable into a first and second energy state. In the scanning process, excitation, de-excitation and detection for the first substance is carried out at a different point in time than for the second substance. This achieves a high spatial resolution beyond the diffraction limit while at the same time a high level of information is provided with physically simple and economical means.

7 Claims, 6 Drawing Sheets

OTHER PUBLICATIONS

"Toward Fluorcence Nanoscopy", Hell, Stefan W, Nature Biotechnology, vol. 21, No. 11, Nov. 2003.

Ultrahigh-resolution Multicolor Colocalization of Single Fluorescent Probes, Lacoste, Thilo D. et al., PNAS, vol. 97, No. 17, 9461-9466, Aug. 15, 2000.

International Bureau, Notification of Transmittal of Translation of the International Preliminary Report on Patentability for PCT/EP2007/058291; 1 page; Jul. 2, 2009.

International Bureau, International Preliminary Report on Patentability for PCT/EP2007/058291;11 pages; Jun. 23, 2009.

* cited by examiner

METHOD AND APPARATUS FOR HIGH-RESOLUTION OPTICAL SCANNING OF A SAMPLE

CROSS-REFERENCE TO RELATED APPLICATION

This application is a national phase based on PCT/EP2007/058291 having a filing date of Aug. 9, 2007 and claims the priority of the German patent application DE 102006047816.9 having a filing date of Oct. 7, 2006. the entire both applications being herewith incorporated by reference.

BACKGROUND OF THE INVENTION

The present invention relates to a method for high-resolution optical scanning of a sample, preferably using a laser scanning fluorescence microscope, the sample encompassing a substance that is shiftable into different energy states (first state Z1 and second state Z2), first state Z1 and second state Z2 differing from one another in terms of at least one optical property; the sample being illuminated, for local generation of first state Z1 of the substance, with light of a wavelength of the excitation spectrum of the substance; the sample being illuminated in a peripheral focus region of the excitation, for generation of second state Z2 of the substance, with light of a suitable de-excitation wavelength; and emitted light that proceeds from the sample and results from a decay of remaining first states Z1 being detected by means of a detection device.

The invention further relates to an apparatus for high-resolution optical scanning of a sample, in particular for carrying out a method according to one of claims 1 to 17, the sample encompassing a substance that is shiftable into different energy states (first state Z1 and second state Z2); first state Z1 and second state Z2 differing from one another in terms of at least one optical property; having at least one light source in order to illuminate the sample, for local generation of first state Z1 of the substance, with light of a wavelength of the excitation spectrum of the substance, and in order to illuminate the sample in a peripheral focus region of the excitation, for generation of second state Z2 of the substance, with light of a suitable de-excitation wavelength; and having a detection device for detecting emitted light that proceeds from the sample and results from a decay of remaining first states Z1.

Methods and apparatuses of the kind in question here have been known for some time from practical use and are used, for example, in the context of STED microscopy. With the imaging optical methods and apparatuses in question, it is possible to achieve spatial resolutions beyond the theoretical limit defined, in accordance with Abbe's law, by the diffraction limit that depends on the wavelength of the light that is used.

In the context of STED microscopy, a substance that is shiftable by light into an excited state, and can be abruptly de-excited from that excited state, is made available for this purpose in the sample being investigated. In STED microscopy, fluorescent dyes are very predominantly used as such substances. In general, the substance is first transferred into the excited state with short-wave light, for example a green laser pulse. The substance is then de-excited in controlled fashion, in a peripheral focus region of the excitation, by means of a long-wave (e.g. red) laser pulse. The de-excitation point function is specifically shaped in order to achieve de-excitation of the substance exclusively in the peripheral focus region. Phase filters are generally used for this purpose; these are located in the beam path of the long-wave laser beam and modify the wavefront of the de-excitation light beam in posi- tionally dependent fashion. What is critical is that the transition from the excited state into the de-excited state, induced by the de-excitation light beam in the peripheral region, take place in saturated fashion, i.e. completely, so that the substance remains in the excited state only in an (in principle, arbitrarily) small central region. The de-excitation light pulse thereby prevents any emission of fluorescent light from the peripheral region of the diffraction-limited excitation spot. The detected fluorescent light thus derives from a narrowly defined sample region whose diameter, because of the saturated de-excitation, can be substantially smaller than allowed by Abbe's law.

Like all other known methods in which an increase in resolution is attained by saturation of a de-excited state, STED microscopy is operated in one-color mode. This means that only one substance, for example only a single fluorescent dye, is made available in the sample. In confocal microscopy, conversely, it is usual to make several different fluorescent dyes available in the sample, and to prepare multi-color images of the sample. It is possible in this fashion to investigate different processes in the sample simultaneously. With multi-color images in the context of conventional microscopy, substantially more information can therefore be obtained (albeit at lower resolution) than is possible with the known spatially high-resolution imaging methods.

SUMMARY OF THE INVENTION

The object underlying the present invention is now to describe a method and an apparatus of the kind cited initially according to which a high spatial resolution beyond the diffraction limit is achieved, simultaneously with a high information yield, with physically simple and economical means.

According to the present invention, the aforementioned object is achieved by a method having the features of claim 1. In accordance therewith, the method is embodied and refined in such a way that the sample encompasses at least one further substance that is transferable into a first state Z1' and into a second state Z2', the substances differing from one another in terms of at least one property and at least partly corresponding in terms of at least one other property, and upon scanning of the sample, the steps of excitation and/or de-excitation and/or detection for the individual substances being carried out separately from one another in time.

The aforementioned object is furthermore achieved by an apparatus having the features of claim 18. In accordance therewith, the apparatus is embodied and refined in such a way that the sample encompasses at least one further substance that is transferable into a first state Z1' and into a second state Z2', the substances differing from one another in terms of at least one property and at least partly corresponding in terms of at least one other property; and that upon scanning of the sample, the steps of excitation and/or de-excitation and/or detection for the individual substances are carried out separately from one another in time.

What has been recognized according to the present invention is firstly that the information resulting from high-resolution optical scanning of a sample can be increased by preparing a multi-color image of the sample. For that purpose, according to the present invention, at least one further substance that is transferable into a first state and into a second state is made available in the sample, the substances differing from one another in terms of at least one property and at least partly corresponding in terms of at least one other property. "Properties" of the substances are to be understood as, for example, their excitation wavelengths or excitation spectra, their emission spectra, de-excitation wavelengths, or lifetimes. The selection according to the present invention of the substances, according to which selection they differ from one another in terms of at least one property, is utilized in order to separate the two substances from one another. The further at least partial correspondence, according to the present invention, in terms of another property enables a particularly simple design, i.e. enables use of the same components or assemblies, for example illumination light sources or detector devices in shared fashion for multiple substances.

It has also been recognized that a simultaneous excitation and simultaneous de-excitation of multiple substances can mean that de-excitation light of the one substance can lead to excitation of another substance. Because of the high power level at which the de-excitation light must be irradiated in order to generate a saturated transition into the de-excited state, a substance excited by a de-excitation wavelength very quickly becomes bleached and is consequently no longer available for an image. In order to circumvent this problem, according to the present invention, upon scanning of the sample, the steps of excitation and/or saturated de-excitation and/or detection for the individual substances are carried out separately from one another in time.

It should be very particularly emphasized at this juncture that the terms "excitation spectrum" or "excitation wavelength" and "de-excitation spectrum" or "de-excitation wavelength" are not to be understood narrowly in the context of the present invention, and that the invention is in no way limited to stimulated emission. The invention instead relates to all methods in which an increase in resolution is generated by saturation of a reversible molecular transition. This also includes, for example, the use of photo-switchable or photo-convertible proteins that can be switched over, by the irradiation of light of specific wavelengths, between fluorescing and non-fluorescing states. In this context, fluorescence is preferably switched on and shut off by way of different wavelength bands, so that an increase in resolution can be attained by saturation of the shut-off state. These types of high-resolution optical imaging methods are referred to very generally as RESOLFT methods. In addition to use of the invention in STED microscopy, the invention can furthermore be utilized in STED 4-pi microscopy, up-conversion microscopy, and in the context of ground state depletion (GSD).

In particularly advantageous fashion, the substances are selected in such a way that the de-excitation spectra of the substances at least partly overlap one another, so that the substances can be transferred into the second state using the same wavelength. With regard to design, it proves advantageous in this context to provide only one common illumination light source for transferring the substances into the second state. Because the illumination light sources used for stimulated de-excitation must generally supply high light power levels and are correspondingly expensive, a considerable reduction in cost can be achieved in this fashion. The excitation spectra for the substances could be different in this case, so that the substances can be excited separately from one another using different wavelengths in each case.

According to a further preferred embodiment, provision can be made that the substances are selected in such a way that the excitation spectra of the substances at least partly overlap one another. In this case, excitation can occur by means of a single illumination light source. One or more illumination light sources can be provided for transferring the substances into the second state.

It is additionally conceivable for the substances to be selected in such a way that the emission spectra of the substances at least partly overlap one another. Such an embodiment proves advantageous in that in this case, detection of the emitted light can be handled particularly easily.

In the context of a concrete embodiment, provision is made that the chronological sequence of the steps of excitation and/or de-excitation and/or detection is defined in accordance with the magnitude of the respective de-excitation wavelengths of the substances. In particularly advantageous fashion, each scanning step begins with the respective substance having the greatest de-excitation wavelength. This procedure has the advantage that the emitted light proceeding from the substance can be detected without influence from another substance. Excitation of the substance by de-excitation light of another substance, said excitation taking place earlier in time than detection of the emitted light, is correspondingly avoided.

Advantageously, the first energy state is a fluorescence-capable state. Fluorescent light is very easy to handle in terms of detection, and many different substances are available with which the sample can be marked.

Because of the low quantum yield of fluorescence, it may in some circumstances be advantageous to carry out multiple excitation, de-excitation, and/or detection cycles, i.e. to carry out the steps of excitation and/or (saturated) de-excitation and/or detection of emitted light several times in succession for one substance, before transitioning to the next substance.

Sequential imaging of the individual substances can be performed in spot-, line-, frame-, or even stack-based fashion. With spot-based imaging, for example, all the substances present in the sample are first investigated in the manner described before the scanning operation is continued at a subsequent spot. With frame-based imaging, a sample region being investigated is first scanned completely, only a first substance being investigated in the manner described. Upon a subsequent complete scan of the sample region being investigated, another substance is exclusively investigated, etc.

In a concrete embodiment, provision can be made that the detection device for detecting the emitted light proceeding from the sample encompasses a detector having a wavelength-dependent element. The wavelength-dependent element can be embodied, for example, as a filter. The detection device can also encompass multiple detectors; in particularly advantageous fashion, one or more detectors of the detection device can be respectively allocated to each substance.

In additionally advantageous fashion, the detectors of the detection device can be shut off individually and/or in groups. It is thereby possible to prevent one substance's emitted light, resulting from excitation of that substance with light of another substance's de-excitation wavelength, from being detected. The shutoff can be provided for the duration of irradiation with the de-excitation wavelength. Alternatively or additionally, detection can be avoided by upstream placement of blocking filters and/or diaphragms.

In the interest of particularly high efficiency, provision can be made that light irradiated in order to generate the de-excited state of one substance is used simultaneously in order to generate the excited state of another substance. Light pulses having a pulse width in the range of 100 ps or longer are preferably used to generate the de-excited state. The photo-damage potential of the de-excitation pulse is thereby minimized.

In the interest of particularly comprehensive avoidance of mutual influence by the individual substances on one another, the substances and the de-excitation wavelengths can be selected, in particularly advantageous fashion, in such a way that the de-excitation wavelengths of the substances lie respectively outside the excitation spectra of the respective remaining substances.

In the interest of great flexibility and good user-friendliness, provision can be made that the excitation and de-excitation wavelengths can be freely selected for each substance. This enables optimal excitation and stimulated de-excitation of the substances. In particularly preferred fashion, a software interface through which a user can select the excitation and de-excitation wavelengths is made available. The wavelengths can, for example, be freely adjusted or inputted by a user. Alternatively or additionally, it is possible to provide a user with a table from which the excitation and/or de-excitation wavelengths can be selected.

There are various ways of advantageously embodying and refining the teaching of the present invention. The reader is referred, for that purpose, on the one hand to the claims and on the other hand to the explanation below of preferred exemplifying embodiments of the invention with reference to the drawings.

BRIEF DESCRIPTION OF THE DRAWINGS

In conjunction with the explanation of the preferred exemplifying embodiments of the invention with reference to the drawings, an explanation will also be given of generally preferred embodiments and refinements of the teaching. In the drawings, in schematic fashion.

DETAILED DESCRIPTION OF THE DRAWINGS

Figure 1:
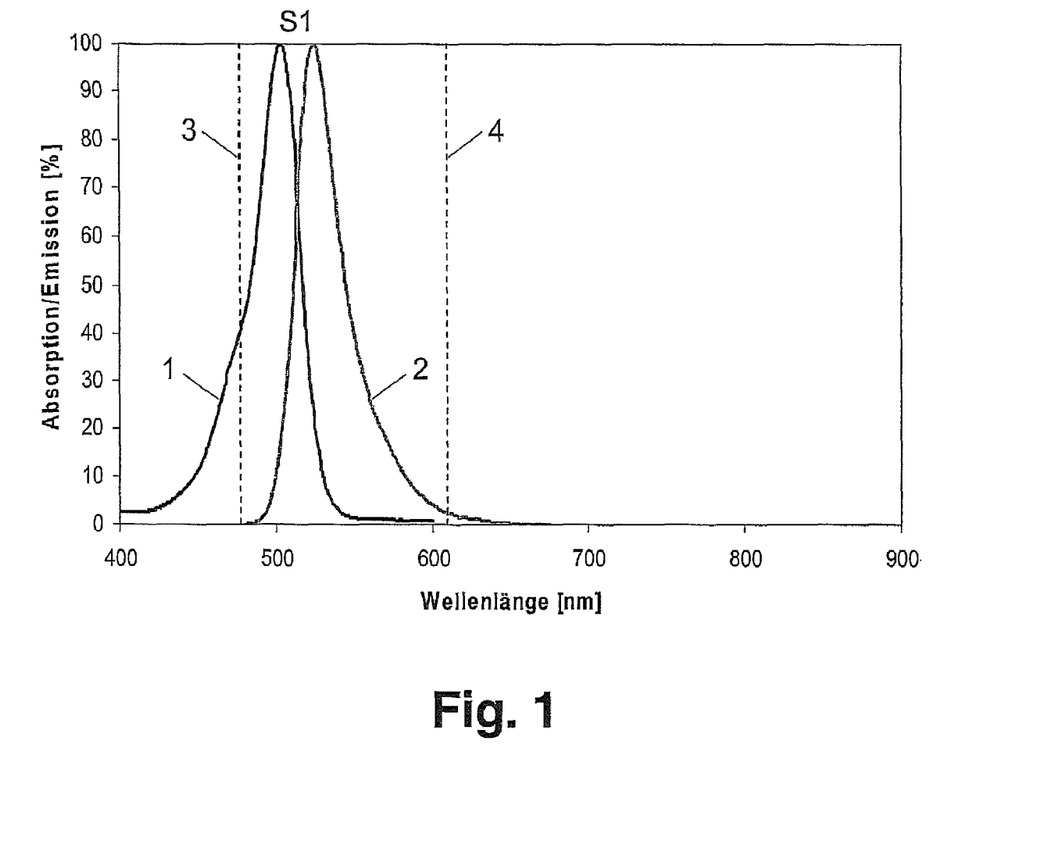
FIG. 1 shows a spectral distribution of an excitation spectrum and an emission spectrum of an individual fluorescent dye.

FIG. 1 shows the spectral distribution of an excitation spectrum 1 and an emission spectrum 2 of a substance S1, this being concretely a fluorescent dye in this case. The use of fluorescent dyes having the spectral distribution shown is typical in one-color STED microscopy according to the known existing art. In this context, a sample to be investigated is illuminated with a short-wave laser pulse of excitation wavelength 3, the pulse preferably deriving from a pulsed laser diode. A de-excitation of the fluorescent molecules at the periphery of the excitation focus is then brought about by injecting a long-wave laser pulse of de-excitation wavelength 4. In order to achieve a de-excitation of the fluorescent molecules exclusively at the focus periphery, the de-excitation spot image function is specially shaped by inserting phase filters, which modify the wavefront of the de-excitation beam in positionally dependent fashion, into the beam path of the long-wave laser beam. De-excitation of the fluorescent molecules is carried out in saturated fashion, so that fluorescent molecules remain in the excited state only in a very small central region. Lastly, the emitted light resulting from spontaneous decay of these remaining excited states is detected with high positional resolution.

Figure 2:
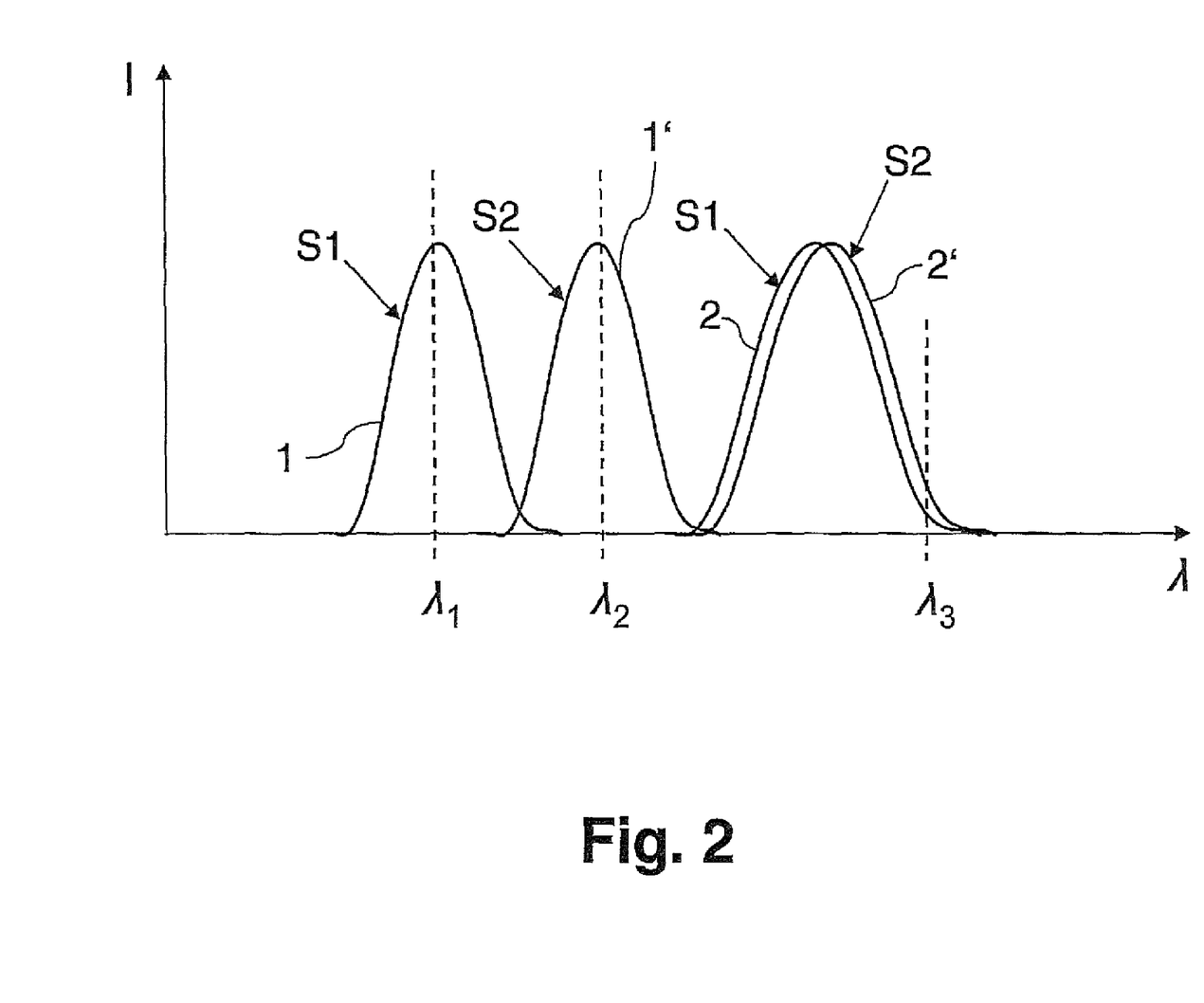
FIG. 2 shows the spectra of two fluorescent dyes that are used in accordance with a first exemplifying embodiment of the method according to the present invention.

FIG. 2 schematically shows excitation spectra 1, 1' and emission spectra 2, 2' of two substances S1 and S2 that can be used in accordance with a first exemplifying embodiment of the method according to the present invention. In the exemplifying embodiment depicted, two fluorescent dyes that are excited with different excitation wavelengths, but are de-excited in stimulated fashion with the same de-excitation wavelength, are used as substances S1, S2.

In order to separate the two dyes, they are excited sequentially, i.e. firstly, for example, the one dye is excited by a laser pulse of wavelength $\lambda_1$, then the dye is de-excited by a laser pulse of wavelength $\lambda_3$. This sequence is repeated several times until sufficient fluorescent light has been collected from that dye. The second dye is then excited by a laser pulse of wavelength $\lambda_2$, and de-excited by a laser pulse of wavelength $\lambda_3$. This second sequence is likewise repeated several times until sufficient fluorescent light has been detected.

Alternatively, it is possible to use a pulse sequence as follows: pulse of wavelength $\lambda_1$, pulse of wavelength $\lambda_3$, pulse of wavelength $\lambda_2$, pulse of wavelength $\lambda_3$, . . . . A pulse train selected in this fashion proves particularly advantageous because it is possible to use therefor laser light sources in which the laser light source of wavelength $\lambda_3$ possess a pulse repetition frequency twice that of the laser light source of wavelengths $\lambda_1$ and $\lambda_2$. Mixtures of the above-described pulse sequences can also be used.

Figure 4:
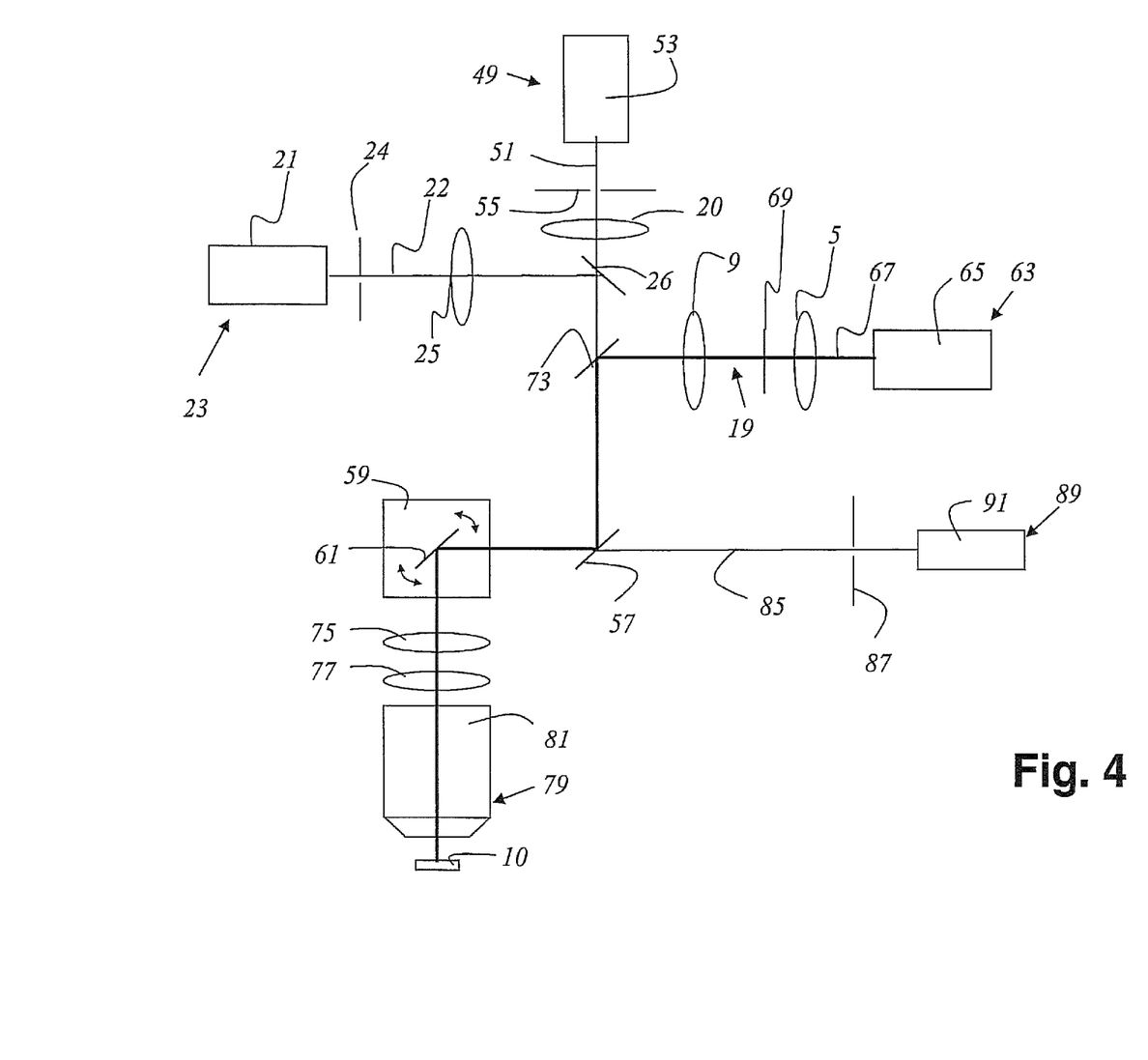
FIG. 4 shows an exemplifying embodiment of an apparatus according to the present invention that is usable in particular in conjunction with the spectral circumstances depicted in FIG. 2.

Sequential imaging of the various color channels can be accomplished, for example, in spot-, line-, frame-, or stack-based fashion. In order to separate the dyes, the pulse train is advantageously synchronized with detection, so that light detected during irradiation of the first sequence can be allocated to the one dye, and light detected during irradiation of the second sequence can be allocated to the second dye. The laser pulses are likewise synchronized with one another. In particular, the excitation and de-excitation pulses belonging to one dye are synchronized with one another. The pulse spacings are, in general, different in the first sequence and in the second sequence. If the emission spectra of the two dyes are spectrally different enough, the fluorescent light can also be separated by means of a wavelength-sensitive element (filter). This then enables, for example, the use of the pulse sequence wavelength $\lambda_1$, wavelength $\lambda_2$, wavelength $\lambda_3$, etc. The laser light source that is used to generate the de-excitation pulses of wavelength $\lambda_3$ must supply a high laser power level in order to achieve saturated de-excitation of the excited states, and is correspondingly relatively expensive. The case described here of a common de-excitation wavelength for both substances S1 and S2 is particularly preferable in that regard, since only one de-excitation laser is required. FIG. 4 shows one possible configuration of a scanning microscope that is coordinated in terms of physical embodiment with the situation described here.

Figure 3:
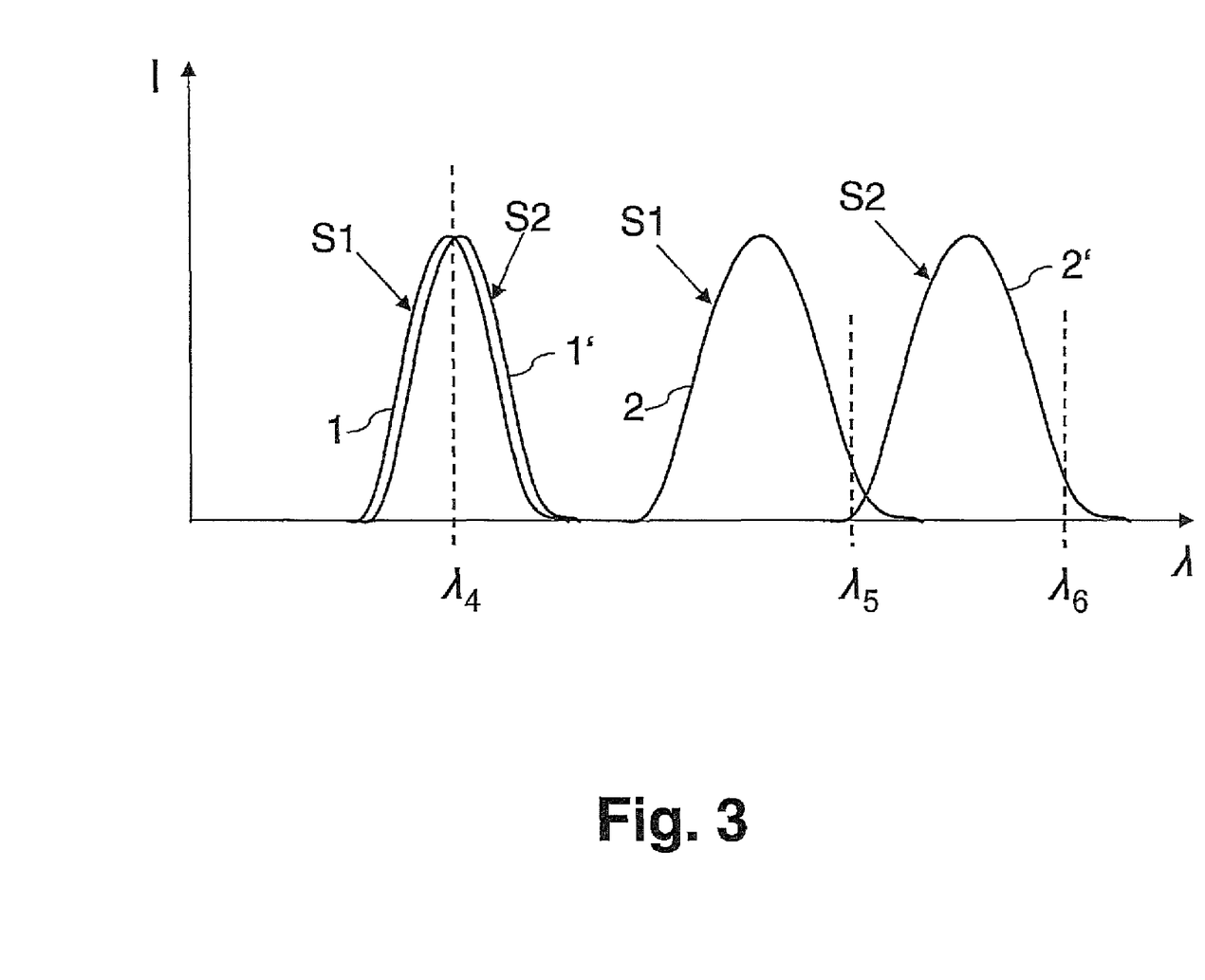
FIG. 3 shows the spectra of two fluorescent dyes that are used in accordance with a second exemplifying embodiment of the method according to the present invention.

In the context of a further exemplifying embodiment that is depicted in FIG. 3, fluorescent dyes selected in such a way that their excitation spectra 1, 1' permit an excitation with the same wavelength $\lambda_4$ in each case are used as substances S1, S2. Conversely, different wavelengths $\lambda_5$ and $\lambda_6$ are used for stimulated de-excitation. If fluorescent spectra 2, 2' of the two dyes are sufficiently different, the fluorescence of the two dyes can then be separated by means of a wavelength-sensitive element (filter), and the respective fluorescence of the two dyes can be recorded using one detector.

Figure 5:
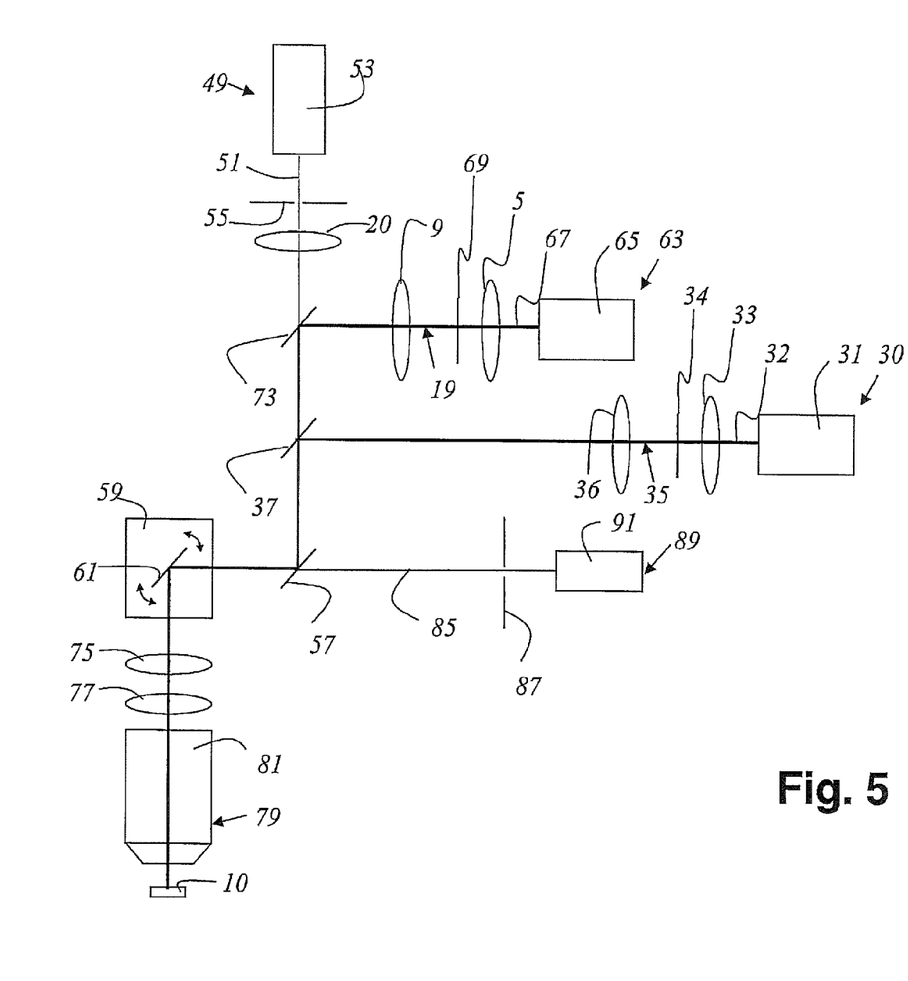
FIG. 5 shows a further exemplifying embodiment of an apparatus according to the present invention that is usable in particular in conjunction with the spectral circumstances depicted in FIG. 3.

Because the lifetimes of the excited states of the two dyes are generally different, it is particularly advantageous to select a different pulse spacing between the excitation pulse and the first de-excitation pulse, and between the excitation pulse and the second de-excitation pulse. The pulses are, in this context, synchronized with one another in time. In particular, the excitation and de-excitation pulses belonging to one dye are synchronized with one another. In addition, the pulse trains can be synchronized with detection. This is useful in particular when fluorescence spectra 2, 2' of the two dyes differ only slightly from one another. The pulse sequence selected is preferably excitation pulse ($\lambda_4$), first de-excitation pulse ($\lambda_5$), second de-excitation pulse ($\lambda_6$), etc. This sequence is repeated several times until sufficient fluorescent light has been collected. FIG. 5 shows one possible configuration of a scanning microscope that is coordinated in terms of physical embodiment with the situation described here.

FIG. 4 schematically depicts an exemplifying embodiment of an apparatus according to the present invention for high-resolution optical scanning of a sample 10 that is marked with two dyes S1 and S2 (not depicted in further detail). The apparatus, embodied as a scanning microscope, is adapted to the use of dyes having a spectral characteristic as depicted in FIG. 2. The scanning microscope encompasses a light source 49, embodied as a pulsed laser 53, that emits a first excitation light bundle 51. Excitation light bundle 51, having a wavelength $\lambda_1$ for excitation of first dye S1, passes through excitation pinhole 55, strikes lens arrangement 20, and is collimated by lens arrangement 20. Excitation light bundle 51 then strikes beam splitters 26 and 73 and main beam splitter 57, which directs excitation light bundle 51 to beam deflection device 59 that encompasses a gimbal-mounted scanning mirror 61.

The scanning microscope further encompasses a second light source 21 that emits a second excitation light bundle 22, having a wavelength $\lambda_2$ for excitation of second dye S2. Second light source 21 is likewise embodied as a pulsed laser 23. After passing through excitation pinhole 24, excitation light bundle 22 strikes optical system 25 and is collimated by optical system 25, and by means of optical element 26 is combined with first excitation light bundle 51.

Lastly, the scanning microscope encompasses a third light source 63, which is embodied as a pulsed laser 65 with which first light source 49 and second light source 21 are synchronized. Third light source 63 emits a light bundle 19 that is referred to hereinafter as stimulation light bundle 67. Stimulation light bundle 67 encompasses light of wavelength $\lambda_3$, with which both dye S1 and dye S2 can be de-excited in stimulated fashion. Stimulation light bundle 67 is collimated by an optical system 5 and strikes a phase filter 69. Stimulation light bundle 67 coming from phase filter 69 strikes dichroic beam splitter 73. Phase filter 69 is imaged by optical system 9 into the pupil of the objective. Dichroic beam splitter 73 combines the two previously merged excitation light bundles 51 and 22, and stimulation light bundle 67, into one common beam path. Stimulation light bundle 67 is also directed by main beam splitter 57 to beam deflection device 59. Beam deflection device 59 sends excitation light bundles 51 and 22, and stimulation light bundle 67, together through scanning optical system 75, tube optical system 77, and focusing optical system 79, namely microscope objective 81, and over or through sample 10.

The focus of excitation light bundles 51 and 22 optically excites sample 10 at a sample point, while the focus of stimulation light bundle 67 de-excites an outer region of the excited sample region in stimulated fashion. The focus of stimulation light bundle 67 is embodied suitably for this, namely as an internally hollow focus. In this variant, phase filter 69 is arranged in a plane (Fourier plane) conjugated with the focal plane of microscope objective 81.

Detected light 85 proceeding from sample 10 travels through microscope objective 81, tube optical system 77, and scanning optical system 75 to beam deflection device 59, from that to main beam splitter 57, passes through the latter and the downstream detection pinhole 87, and lastly arrives at detection device 89, which is embodied as a multiband detector 91. Detector 91 generates electrical signals proportional to the light output of detected light 85, which signals, together with the position signals of beam deflection device 59, are forwarded to a processing unit (not shown) for image display.

FIG. 5 shows a further exemplifying embodiment of a scanning microscope according to the present invention for two dyes S1 and S2, which is adapted to a spectral characteristic of the dyes as depicted in FIG. 3. The scanning microscope depicted in FIG. 5 is very similar to the scanning microscope depicted in FIG. 5. Identical components are identified with the same reference characters. Unlike the scanning microscope according to FIG. 5, the scanning microscope depicted here comprises only one light source 49 for generating an excitation light bundle 51. Excitation light bundle 51 encompasses light having a wavelength 4, which serves both to excite first dye S1 and to excite second dye S2.

Like the scanning microscope according to FIG. 4, the scanning microscope according to FIG. 5 also encompasses a light source 63, which is embodied as a pulsed laser 65 that is synchronized with first light source 49. Second light source 63 emits a light bundle 19 that is referred to hereinafter as stimulation light bundle 67. In this case, stimulation light bundle 67 encompasses light of wavelength $\lambda_5$ with which first dye S1 is de-excited in stimulated fashion. Stimulation light bundle 67 is collimated by an optical system 5 and strikes a phase filter 69.

The scanning microscope additionally encompasses a third light source 30 that is embodied as a pulsed laser 31 with which light source 49 is synchronized. Third light source 30 emits a light bundle 35 that is referred to hereinafter as stimulation light bundle 32. Stimulation light bundle 32 encompasses light of wavelength $\lambda_6$, with which second dye S2 is de-excited in stimulated fashion. Stimulation light bundle 32 is collimated by an optical system 33 and strikes a phase filter 34. The stimulation light bundles 67 and 32 coming from phase filters 69 and 34 are deflected by dichroic beam splitters 73 and 37. Phase filters 69 and 34 are imaged by optical systems 9 and 36 into the pupil of the objective. The beam bundles are directed by main beam splitter 57 to beam deflection device 59. Beam deflection device 59 sends excitation light bundle 51 and stimulation light bundles 67 and 32 together through scanning optical system 75, tube optical system 77, and focusing optical system 79, namely microscope objective 81, and over or through sample 10.

With regard to the focus points of excitation light bundle 51 and of stimulation light bundles 67 and 32, and with regard to the detection of detected light 85, the statements already made above in conjunction with FIG. 4 also apply here.

By aligning optical systems 20, 25, 5, and 33 in an axial direction, the longitudinal chromatic aberration of objective 81 can be compensated for and the excitation and de-excitation foci can be superimposed.

Figure 6:
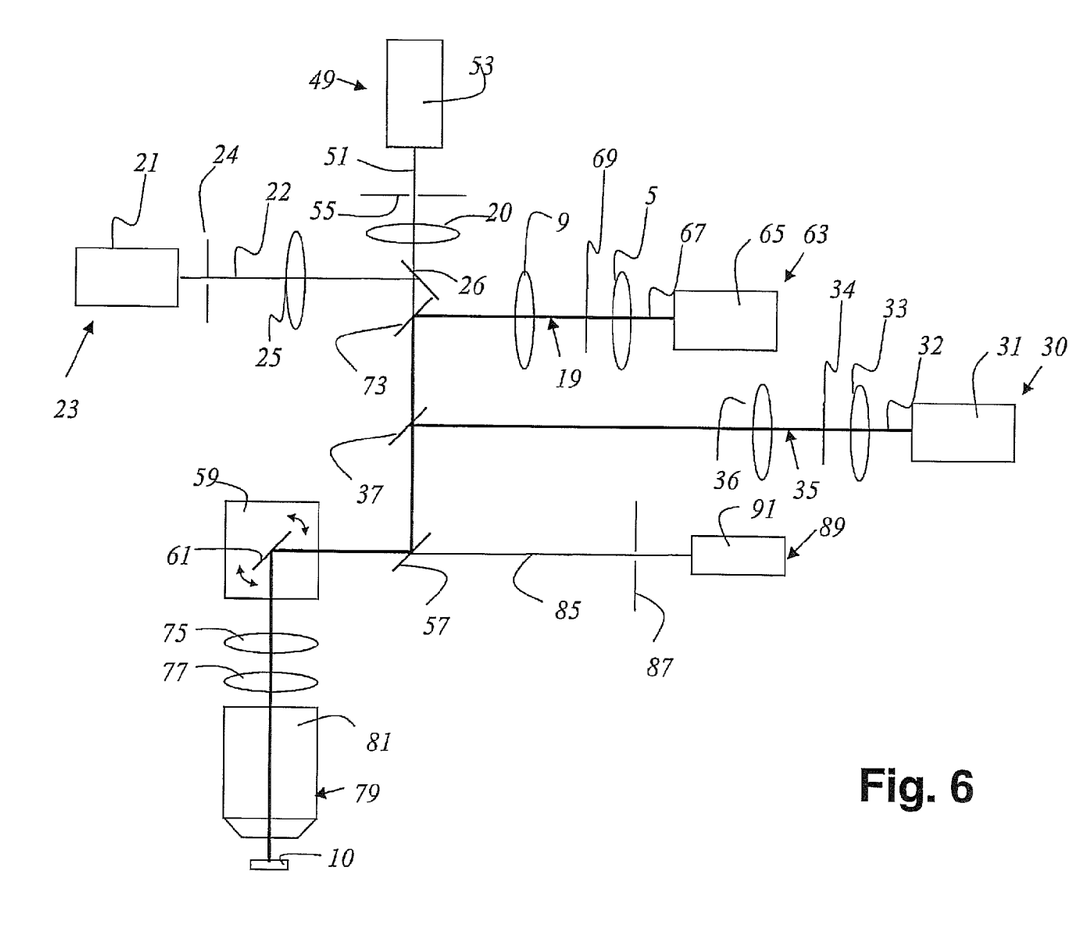
FIG. 6 shows an exemplifying embodiment of an apparatus according to the present invention with separate excitation and separate de-excitation of two fluorescent dyes.

Lastly, FIG. 6 shows an exemplifying embodiment of a scanning microscope according to the present invention whose configuration corresponds very largely to the configuration of the scanning microscopes shown in FIGS. 4 and 5. The only difference is that two separate light sources 49 and 23 are provided for excitation of the two substances S1 and S2, and two separate light sources 63 and 30 are also provided for stimulated de-excitation.

In order to avoid repetition, reference is made to the general portion of the description and to the appended Claims with regard to further advantageous embodiments of the apparatus.

In conclusion, be it noted expressly that the exemplifying embodiments of the apparatus according to the present invention that are described above serve merely for discussion of the teaching claimed, but do not limit it to the exemplifying embodiments.

The invention claimed is:

1. A method for high-resolution optical scanning of a sample comprising:
a first substance that is switchable into at least a first energy state and a second energy state differing from the first energy state in terms of at least one optical property;
a second substance that is switchable into at least a first energy state and a second energy state differing from the first energy state in terms of at least one optical property; wherein the first and second substances differ from one another in at least one property and are at least partly the same in at least one other property,
said method comprising the method steps of:
illuminating a first area of the sample in an excitation step with illumination light of a wavelength of an excitation spectrum of the first and second substances for local generation of the first energy state of the first and second substances;
illuminating a second area of the sample extending peripherally around a focus region of the excited first area in a de-excitation step with illumination light of a suitable de-excitation wavelength for generating the second energy state of the first and second substances;
detecting emitted light by means of a detection device, said light being emitted from the sample as a result from a decay of remaining first energy state;
scanning of the sample such that at least one of the steps of excitation, de-excitation and detection for the first substance is carried out at a different point in time than for the second substance; and
using the illumination light for generating the de-excited state of one of the first or second substances simultaneously for generating the excited state of the other one of said second or first substances.

2. The method according to claim 1, further comprising the method step of selecting the first and second substances such that the de-excitation spectra of the first and second substances at least partly overlap one another.

3. The method according to claim 1, further comprising the method step of selecting the first and second substances such that the excitation spectra of the substances at least partly overlap one another.

4. The method according to claim 1, further comprising the method step of selecting the first and second substances such that the emission spectra of the substances at least partly overlap one another.

5. The method according to claim 1, wherein the distance of time of at least one of the excitation, de-excitation and detection steps is defined in accordance with the magnitude of the respective de-excitation wavelengths of the substances.

6. The method according to claim 5, wherein each scanning step begins with the respective substance having the longest de-excitation wavelength.

7. The method according to claim 1, further comprising the method step of suppressing during illumination of the sample with a de-excitation wavelength of the first substance the detection of light emitted by the second substance whose excitation spectrum encompasses the irradiated de-excitation wavelength of the first substance.

* * * * *